US007235395B2

(12) United States Patent
Stadler et al.

(10) Patent No.: US 7,235,395 B2
(45) Date of Patent: *Jun. 26, 2007

(54) LACTIC ACID BACTERIA AS AGENTS FOR TREATING AND PREVENTING ALLERGY

(75) Inventors: Beda M. Stadler, Bern (CH); Monique Vogel, Bern (CH); Edouard-Jacques Germond, Crissier (CH); Rodolphe Fritsche, Lausanne (CH)

(73) Assignee: Nestec S.A., Vevey (CH)

( * ) Notice: Subject to any disclaimer, the term of this patent is extended or adjusted under 35 U.S.C. 154(b) by 275 days.

This patent is subject to a terminal disclaimer.

(21) Appl. No.: 10/652,502

(22) Filed: Aug. 29, 2003

(65) Prior Publication Data
US 2004/0265290 A1  Dec. 30, 2004

Related U.S. Application Data

(63) Continuation of application No. PCT/EP02/02326, filed on Mar. 4, 2002.

(51) Int. Cl.
*C12N 15/74* (2006.01)
*C12N 15/62* (2006.01)
*C12N 1/21* (2006.01)
*A61K 39/00* (2006.01)

(52) U.S. Cl. ............... 435/252.3; 435/69.7; 435/252.9; 424/93.2; 424/93.4; 424/93.45; 536/23.3

(58) Field of Classification Search ................ None
See application file for complete search history.

(56) References Cited

U.S. PATENT DOCUMENTS

| 5,242,821 | A | | 9/1993 | Palva et al. ............... 435/252.3 |
|---|---|---|---|---|
| 5,559,007 | A | | 9/1996 | Suri et al. ................. 435/252.3 |
| 6,133,023 | A | * | 10/2000 | Madsen et al. ............ 435/320.1 |
| 6,190,662 | B1 | * | 2/2001 | Steidler et al. .......... 424/184.1 |
| 6,642,011 | B2 | * | 11/2003 | Estell ......................... 435/7.24 |
| 6,737,521 | B1 | * | 5/2004 | Fischetti et al. ........... 536/23.4 |
| 6,835,550 | B1 | * | 12/2004 | Estell et al. ................ 435/7.24 |
| 7,060,462 | B2 | * | 6/2006 | Pan ............................ 435/69.1 |
| 2002/0048816 | A1 | * | 4/2002 | Deblaere et al. ............ 435/485 |
| 2002/0137140 | A1 | * | 9/2002 | Vrang et al. ............... 435/69.1 |
| 2004/0071714 | A1 | * | 4/2004 | Germond et al. ........ 424/184.1 |

FOREIGN PATENT DOCUMENTS

| JP | 9234078 | 9/1997 |
|---|---|---|
| WO | WO 92/04451 | 3/1992 |
| WO | WO 93/11220 | 6/1993 |
| WO | WO 96/32486 | 10/1996 |
| WO | WO 96/32487 | 10/1996 |
| WO | WO 97/09437 | 3/1997 |
| WO | WO 97 31948 A | 9/1997 |
| WO | WO 98/10079 | 3/1998 |
| WO | WO 00 63252 A | 10/2000 |

OTHER PUBLICATIONS

Gilbert, C., et al., 1996, A new cell surface proteinase: Sequencing and analysis of the prtB gene from *Lactobacillus delbrueckii* subsp. bulgaricus, Journal of Bacteriology, vol. 178, No. 11, pp. 3059-3065.*

(Continued)

*Primary Examiner*—Kathleen Kerr Bragdon
*Assistant Examiner*—William W. Moore
(74) *Attorney, Agent, or Firm*—Bell, Boyd & Lloyd LLP

(57) ABSTRACT

The present invention pertains to novel strains of lactic acid bacteria capable of reducing an individual's tendency to react allergic against a variety of different allergens. In particular, the present invention relates to recombinant strains of lactic acid bacteria that express surface polypeptides which include peptides or antibody fragments acting as mimic for at least a part of the $F_c$ region of IgE-molecules. The invention also pertains to food or pharmaceutical compositions containing said micro-organisms or active fractions thereof.

**

OTHER PUBLICATIONS

Boersma et al., XP002027111, L:actobacillus As Vectors With Intrinsic Adjuvanticity For Safe Live Mucosal Vaccines: Journal of Cellular Biochemistry, vol. 19A, no. suppl. pp. 255 (1995).

Pouwels et al., XP000921209 "The potential of *Lactobacillus* as a carrier for oral immunization: Development and preliminary characterization of vector systems for targeted delivery of anitgens," Journal of Biotechnology, NL, Elsevier Science Publishers. Amsterdam , pp. 183-192, vol. 44, No. 1 (1996).

Todd R. Klaenhammer, "Genetics of Intestinal Lactobacilli", Southeast Dairy Foods Research Center and Department of Food Science, North Carolina, Elsevier Science Limited, Int. Dairy Journal 5, pp. 1019-1058, (1995).

Oscar P. Kuipers, Pascafle G. G. A. de Ruyter, Michiel Kleerebezem and Wifiem M, de Vos, "Controlled Overproduction Of Proteins By Lactic Acid Bacteria", Elsevier Science Limited, TIBTECH, vol. 15,5, pp. 135-140, (1997).

M.van Asseldonk, "Dissertation Abstracts, Production and Secretion of Heterologous Proteins by *Lactococcus lactis*", Netherlands Milk & Dairy Journal 48, pp. 111-116. (1994).

C. Rush . L. Hafner P. Timms, "Protein A as a fusion partner for the expression of heterologous proteins in *Lactobacillus*", Appl. Microbiol Biotechnol, vol. 47, pp. 537-542 (1997).

\* cited by examiner

LACTIC ACID BACTERIA AS AGENTS FOR TREATING AND PREVENTING ALLERGY

CROSS-REFERENCE TO RELATED APPLICATIONS

The present application is a continuation of International Application PCT/EP02/02326 filed Mar. 4, 2002, the entire content of which is expressly incorporated herein by reference thereto.

BACKGROUND

The present invention pertains to novel strains of lactic acid bacteria capable of reducing an individual's tendency to develop allergic reactions. In particular, the present invention relates to recombinant strains of lactic acid bacteria expressing surface polypeptides which include small and larger peptides acting as mimics for at least a part of the $F_c$ region of immunoglobulin E (IgE)-molecules. The invention also pertains to food or pharmaceutical compositions containing said micro-organisms or active fractions thereof.

The immune system is a complex and multifactorial defense system that protects the body from any invasive biological or chemical agent, such as viruses, bacteria, parasites and fungi or simply larger chemical substances. Although being indispensable for maintaining the body's integrity, the immune system may in certain cases be the cause of the illness itself, such as in autoimmune diseases, inflammation or allergies.

Allergies are inappropriate reactions of the immune system to a variety of substances (allergens). Generally, individuals do not generate a significant immune reaction against substances regularly encountered in the environment, such as pollen or food material, which non-reactivity is deemed to be mainly due to a suppressing mechanism of the immune system itself However, in an impaired condition the immune system does not fulfil said suppressing activity resulting in a specific immune reaction against the allergen—the allergic reaction.

A generally established mechanism of allergic reactions involves a sequence of events beginning with the uptake of the allergen which needs to pass the epithelial barrier to reach and activate effector cells, located in the lamina propria or epithelium below the level of the tight junctions. The clinical symptoms associated with allergic reactions are basically the result of an early specific immune response and a late inflammatory reaction. During the early phase immunoglobulines E (IgE) against the allergenic substance are produced by the host's immune system, which are subsequently bound via a receptor protein to e.g. mast cells and basophils. Upon binding and crosslinking the IgE molecules on their surface the cells release histamine and cytokines, which then mediate the late phase by recruiting inflammatory cells into the nasal and upper respiratory tract passages. The influx of eosinophils, macrophages, lymphocytes, neutrophils and platelets subsequently starts the inflammatory cycle amplifying the initial immune response which in turn triggers the release of more inflammatory cells.

In the past, the number of individuals suffering from allergy has increased, which is frequently attributed to an ever increasing atmospheric pollution caused by e.g. exhaust gases. Also, an extended consumption of proteinaceous material is deemed to contribute to said development, in particular to the growing occurrence of food allergy. Further, the deficit in microbial infections encountered in developed countries has also been suggested as another possible cause for the increase of atopic diseases.

Therefore, there exists a need in the art to treat allergy, for which different approaches have been proposed so far.

As for the treatment of food allergy some methods rely on modifying the food material itself such that its allergenic potential is reduced. This may be achieved by altering the chemical structure thereof, or by limiting or banning the food material or components thereof, respectively, which would be the cause of such trouble. Yet, a problem involved often resides in that the specific allergenic substance in the respective food material is frequently not known so that in most cases it is not clear which component should be selectively removed or altered.

A different approach of treating food allergy and food intolerance is directed to restoring and maintaining the intestine's integrity such that food allergens essentially may not pass. In this respect, U.S. Pat. No. 5,192,750 describes the use of N-acetyl glucosamine to enable the mucosa to form the necessary barrier to transmission of food allergens and to maintain normal function.

A most general approach of treating allergy is an immunotherapy which involves repeated injection of the allergen, over a period of several years, to desensitize a patient to the allergen. Proceeding accordingly is, however, time consuming, involves years of treatment, and often fails to achieve its goal of desensitizing the patient.

According to a more recent approach, vaccination of individuals against IgE molecules is suggested which inhibits triggering of mast cells and basophils. To this end, WO 97/31948 proposes specific peptides for vaccination that resemble in their three dimensional conformation parts of the IgE molecule, i.e. the immunoglobulines involved in the release of mediators, that play a part in the regulation of allergic and inflammatory reactions. It is conceived that the individual's own immune system will eventually form antibodies directed to said IgE molecules such that said IgE immunoglobulines are scavenged.

However, said method harbours the disadvantage common to normal vaccination procedures in that the biologically active substance has to be administered by invasive methods, such as e.g. by intravenous injection, which route of administration is generically disliked by patients. On the other hand, when choosing the oral route, suitable galenic formulas have to be designed to allow the biologically active substance to pass the gastro-intestinal tract without getting destroyed. Another problem encountered in this method resides in that the mimotopes are, in most of the cases, short length peptides, that on their own will not elicit a substantial immune response so that apart from carriers and excipients adjuvantia have to be included in the composition.

Therefore, there is a need in the art to provide improved means for treating allergy. In particular, an object of the present invention resides in providing means that allow treatment of allergy in an efficient, easy and cost effective manner preferably without requiring a physician and without bringing about the negative associations linked with such treatments.

SUMMARY OF THE INVENTION

The present invention now resolves these problems by providing novel lactic acid bacteria strains that express on their surface a polypeptide containing at least one peptide sequence mimicking at least part of a conformational epitope (mimotope) of an IgE molecule. The bacterial strain is preferably selected from *Lactobacillus* group or *Bifido-* bacterium group or *Lactococcus* group, and is more preferably derived from the groups of *L. acidophilus, L. johnsonii, L. gasseri, L. casei, L. paracasei* or *L. reuteri*.

Preferably, the bacterial strain is included in a food composition, such as a milk, yoghurt, curd, cheese, fermented milks, milk based fermented products, ice cream, fermented cereal based products, milk based powders, infant formulae or pet food, wherein the bacterial strain is contained therein in an amount ranging from $10^7$ to $10^{12}$ cfu (colony formation unit) per dosage form.

The invention also relates to a method of making an ingestible carrier for the treatment of allergy or prevention of the onset of allergic reactions which comprises adding a bacterial strain as described herein to a suitable carrier. In particular, the suitable carrier is a food composition such as one of those mentioned herein.

Yet another embodiment of the invention relates to a method for the treatment of allergy or prevention of the onset of allergic reactions which comprises administering to a subject in need of such treatment one of the ingestible carriers or food compositions disclosed herein. The subjects are typically mammals such as humans or animals.

BRIEF DESCRIPTION OF THE DRAWINGS

The accompanying drawings, which are incorporated in and form a part of the specifications, illustrate the preferred embodiments of the present invention, and together with the description serve to explain the principles of the invention. In the drawing figures.

DETAILED DESCRIPTION OF THE PREFERRED EMBODIMENTS

Figure 1:
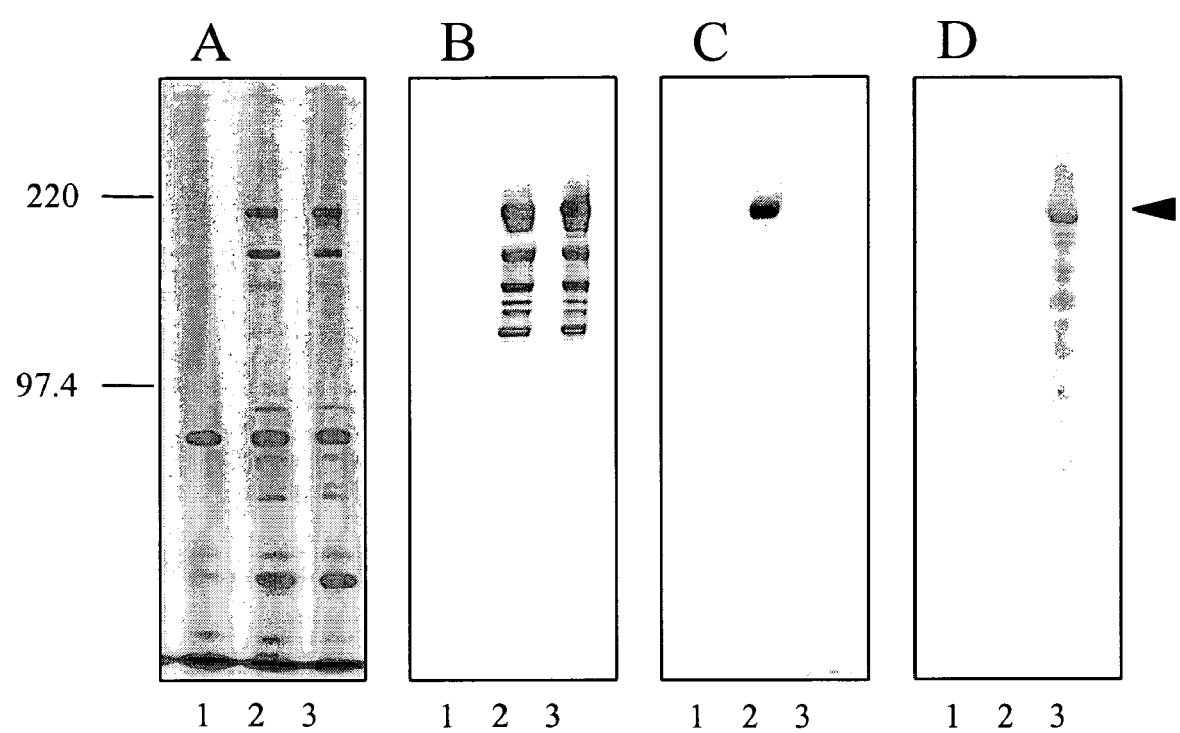
FIG. 1 shows a protein stain and Immunoblot analysis of *Lactobacillus johnsonii* recombinants. (A) Protein stain of La1 wild type (lane 1), La1 carrying pMD112TT (La1TT, lane 2) or pMD112ε4 (La1ε4, lane 3). (B) Expression of proteinase PrtB (SEQ ID NO:2) on La1TT (lane 2) and La1ε4 (lane 3). Approximately $10^8$ bacteria were analyzed by immunoblot using anti-PrtB serum diluted 1:2000. Wild type La1 was loaded as a negative control (lane 1). Binding antibodies were detected with horseradish peroxidase conjugated goat anti-rabbit IgG (Fc) antibodies. (C) Expression of tetanus mimotope on the surface of La1TT (lane 2). Approximately $10^8$ bacteria per slot were analyzed by immunoblot using anti-TT serum diluted 1:1000. La1 (lane 1) and La1ε4 (lane 3) were used as negative controls. Binding antibodies were detected with horseradish peroxidase conjugated goat anti-rabbit IgG (Fc) antibodies. (D) Expression of ε4 mimotope on the surface of La1ε4 (lane 3). Approximately $10^8$ bacteria per slot were analyzed by immunoblot using anti-ε4 serum (SDS280) at a concentration of 10 µg/ml. La1 (lane 1) and La1TT (lane 2) were used as negative controls. Binding antibodies were detected with horseradish peroxidase conjugated goat anti-rabbit IgG (Fc) antibodies. The arrow indicates the height of the proteinase band seen in A-D.

In the studies leading to the present invention it has now been found that by providing a lactic acid bacterium containing a recombinant surface polypeptide comprising a peptide sequence as defined above a specific immunization of an individual against IgE may be obtained, with the result that allergic reactions of said individuals to essentially all antigens are suppressed.

Without wishing to be bound to any theory it is presently envisaged that the lactic acid bacteria, that upon ingestion remain in the gastro-intestinal tract for a period of time, are capable of presenting the antigen to an individual's immune system such that an effective immune reaction takes place leading to the formation of anti-IgE antibodies in the individual. This fact is all the more surprising, since it could not be predicted, whether administration of a bacterium to an individual, which is effected via the gastro-intestinal route, containing such a surface protein, would eventually present the corresponding antigen—the mimotope—to the individual's immune system such that the immune system will be capable of recognizing the antigen and elicit an immune response thereto. What is more, the biological environment, wherein the mimotope is presented to the immune system is such that the use of adjuvantia for eliciting an immune response against the antigen is not required.

According to a preferred embodiment the lactic acid bacterium containing a surface polypeptide containing the mimotope belongs to the *Lactobacillus* group or *Bifidobacterium* group or *Lactococcus* group, and is more preferably derived from the groups of *L. acidophilus, L. johnsonii, L. gasseri, L. casei, L. paracasei* or *L. reuteri*, all of human or animal origin. According to a more preferred embodiment the lactic acid bacterium is a probiotic lactic acid bacterium. As probiotics micro-organisms shall be understood capable to pass the gastro-intestinal tract in an essentially viable and live form and optionally also be capable of stimulating the host's immune system. According to a most preferred embodiment the lactic acid bacteria is *Lactobacillus johnsonii*.

The nature of the surface polypeptide is not crucial with the proviso that the "mimotope peptide sequence" may be inserted such that it is accessible for the immune system. According to a preferred embodiment the surface polypeptide/protein, into which a sequence mimicking a conformational epitope of an IgE immuno-globuline is inserted, is the cell surface anchored protease of *Lactobacillus bulgaricus* the sequence of which was published in Gilbert et al., (1996) J. Bacteriol, 178, 3059-3065. This protein was characterized as a 2000 amino acids protein, being composed of a leader peptide of 33 amino acids (pre-region) responsible for cell export of the enzyme, followed by a series of 154 amino acids (pro-region) which is responsible, upon cleavage, for the activation of the proteolytic activity of the enzyme and 700-800 amino acids for the active site. The subsequent region (around 1000 amino acids) has been suggested to play a role in the specificity of cleavage and transport in the cell of the generated peptides and to also span the cell wall. The protease is cell wall anchored by its carboxyl end with the last 200 amino acids being responsible for the specific covalent binding to the cell wall peptidoglycan structure.

The polypeptide may be expressed in the lactic acid bacterium according to methods well known in the art. For example the commercially available vectors pNZ124 (Platteuw et al., (1994) Appl. Env. Microbiol. 60, 587), pGK12 (Walke et al., (1996) FEMS Microbiol. 138, 233,) or pG+host9 (Maguin et al., (1996) J. Bacteriol 178, 931) may be used for episomal expression. Yet, having in mind the superior stability of chromosome integration, this way of doing could be preferred for the recombinant gene coding for the respective polypeptide. For integration into the chromosome homologous recombination may be applied by e.g. using an recombinant gene from lactic acid bacteria, containing the tolerogenic peptide and replacing the endogenous gene. Yet, methods for introducing recombinant genes into a host's chromosome are well within the skilled person's skill.

The peptide sequences (SEQ ID NOS: 1-17) and the anti-idiotypic VH and VL sequence (SEQ ID NOS: 18-19) mimicking a conformational epitope of an IgE may be found by screening random peptide and human Fab antibodies phage display libraries with an antibody directed to the Fc part of IgE. Preferred mimotope and anti-idiotypic Fab sequences are selected from the group consisting of:

Ile-Asn-His-Arg-Gly-Tyr-Trp-Val, (A) (SEQ ID NO:1)

Arg-Asn-His-Arg-Gly-Tyr-Trp-Val, (B) (SEQ ID NO:2)

Arg-Ser-Arg-Ser-Gly-Gly-Tyr-Trp-Leu-Trp, (C) (SEQ ID NO:3)

Val-Asn-Leu-Thr-Trp-Ser-Arg-Ala-Ser-Gly, (D) (SEQ ID NO:4)

Val-Asn-Leu-Pro-Trp-Ser-Arg-Ala-Ser-Gly, (E) (SEQ ID NO:5)

Val-Asn-Leu-Thr-Trp-Ser-Phe-Gly-Leu-Glu, (F) (SEQ ID NO:6)

Val-Asn-Leu-Pro-Trp-Ser-Phe-Gly-Leu-Glu, (G) (SEQ ID NO:7)

Val-Asn-Arg-Pro-Trp-Ser-Phe-Gly-Leu-Glu, (H) (SEQ ID NO:8)

Val-Lys-Leu-Pro-Trp-Arg-Phe-Tyr-Gln-Val, (I) (SEQ ID NO:9)

Val-Trp-Thr-Ala-Cys-Gly-Tyr-Gly-Arg-Met, (J) (SEQ ID NO:10)

Gly-Thr-Val-Ser-Thr-Leu-Ser, (K) (SEQ ID NO:11)

Leu-Leu-Asp-Ser-Arg-Tyr-Trp, (L) (SEQ ID NO:12)

Gln-Pro-Ala-His-Ser-Leu-Gly, (M) (SEQ ID NO:13)

Leu-Trp-Gly-Met-Gln-Gly-Arg (N) (SEQ ID NO:14)

Leu-Thr-Leu-Ser-His-Pro-His-Trp-Val-Leu-Asn-His-Phe-Val-Ser, (O) (SEQ ID NO:15)

Ser-Met-Gly-Pro-Asp-Gln-Thr-Leu-Arg, (P) (SEQ ID NO:16)

Val-Asn-Leu-Thr-Trp-Ser, (Q) (SEQ ID NO:17)

Gln-Val-Lys-Leu-Leu-Glu-Ser-Gly-Pro-Gly-Leu-Val-Lys-Pro-Ser-Glu-Thr-Leu-Ser-Leu-Thr-Cys-Thr-Val-Ser-Gly-Gly-Ser-Ile-Ser-Ser-Gly-Gly-Tyr-Tyr-Trp-Thr-Trp-Ile-Arg-Gln-Arg-Pro-Gly-Lys-Gly-Leu-Glu-Trp-Ile-Gly-Tyr-Ile-Tyr-Tyr-Ser-Gly-Ser-Thr-Ser-Tyr-Asn-Pro-Ser-Leu-Lys-Ser-Arg-Val-Thr-Met-Ser-Val-Asp-Thr-Ser-Lys-Asn-Gln-Phe-Ser-Leu-Arg-Leu-Thr-Ser-Val-Thr-Ala-Ala-Asp-Thr-Ala-Val-Tyr-Tyr-Cys-Ala-Arg-Glu-Arg-Gly-Glu-Thr-Gly-Leu-Tyr-Tyr-Pro-Tyr-Tyr-Tyr-Ile-Asp-Val-Trp-Gly-Thr-Gly-Thr-Thr-Val-Thr-Val-Ser-Ser (R) (SEQ ID NO:18)

-continued

Glu-Leu-Val-Val-Thr-Gln-Pro-Ala-Ser-Val- (S)(SEQ ID NO: 19)

Ser-Gly-Ser-Pro-Gly-Gln-Ser-Ile-Thr-Ile-

Ser-Cys-Thr-Gly-Thr-Arg-Ser-Asp-Val-Gly-

Gly-Tyr-Asn-Tyr-Val-Ser-Trp-Tyr-Gln-Gln-

His-Pro-Gly-Lys-Ala-Pro-Lys-Leu-Met-Ile-

Tyr-Asp-Val-Ser-Asn-Arg-Pro-Ser-Gly-Val-

Ser-Asn-Arg-Phe-Ser-Gly-Ser-Lys-Ser-Gly-

Asn-Thr-Ala-Ser-Leu-Thr-Ile-Ser-Gly-Leu-

Gln-Ala-Glu-Asp-Glu-Ala-Asp-Tyr-Tyr-Cys-

Ser-Ser-Tyr-Thr-Ser-Ser-Ser-Thr-Leu-Gly-

Val-Phe-Gly-Gly-Gly-Thr-Lys-Leu-Thr-Val-

Leu-Gly

For more detailed information regarding the isolation and/or preparation of peptide and anti-idiotypic VH and VL sequences mimicking part of an IgE constant region in general, reference is made to WO 97/31948, the teaching of which is expressly incorporated herein by reference thereto.

The present invention also relates to a food and pharmaceutical composition, in particular vaccines, containing at least one such lactic acid bacterium as described above.

The bacterial strain may be included in the composition in an amount ranging from $10^5$ to $10^{12}$ cfu/g of the material. The food composition may be milk, yoghurt, curd, cheese, fermented milks, milk based fermented products, ice cream, fermented cereal based products, milk based powders, infant formulae or, in case of animals, pet food and the pharmaceutical composition may be in the form of tablets, liquid bacterial suspensions, dried oral supplements, wet oral supplements, dry tube feeding or wet tube-feeding.

The lactic acid bacterium and the food/pharmaceutical composition of the present invention may be used for treating any disease condition associated with allergic reactions, wherein an immune reaction involving IgE antibodies are involved, such as e.g. rhinitis, atopic dermatitits, erythema etc. Likewise, it will be appreciated that the bacteria/compositions of the present invention are well suited for being used as a "vaccination agent", preventing the onset of allergy in an individual in general. This may easily be accomplished by simply feeding the person in need of a treatment against allergy with a food composition or a pharmaceutical composition according to the present invention. Upon ingestion the bacteria will colonize the intestine for a certain period of time so that depending on the amount of bacterial cell counts and the time period during which the compositions of the present invention are administered, the mimotope is presented to he individual, so that he may form an immune response against the mimotope(s). It will be appreciated that in addition to the lactic acid bacterium contained in the compositions of the present invention agents known to stimulate the immune system may be administered as well, so as to improve the immune response against the mimotope.

EXAMPLES

The following examples further illustrate the invention without limiting it thereto.

Example 1

Construction of Recombinant Polypeptide

Two peptides were fused with the cell surface anchored protease of *L. bulgaricus* to be displayed on the surface of the bacterium La1, i.e. the peptide ϵ4 and another peptide (used as a control) derived from Tetanus Toxin (termed TT in the following sequence, see below).

The mimotope (ϵ4) was fused in frame to the cell surface proteinase (PrtB) from *Lactobacillus bulgaricus* (Gilbert et al., (1996) J. Bacteriol, 178, 3059-3065).

The protease gene was first amplified with its promoter by using the following two primers:

5'-TTTTGTGGATCCTTAACTTCATAGCACG-3'  (SEQ ID NO:20)
(upstream the promoter of the gene,
carrying a BamHI site)

5'-ATATTATCTAGAATTGAATAGATTGCC-3'  (SEQ ID NO:21)
(downstream the rho-independent
terminator of the gene, carrying a
XbaI site)

The amplification product was cleaved with BamHI and XbaI and cloned in the lactic acid bacteria vector pNZ124, that had been digested with the same restriction enzymes, and eventually introduced by electroporation into plasmid-free (beta-galactosidase and protease negative) *Lactococcus lactis*.

The region of the active site of the cloned protease was replaced by the sequence of the TT and the ϵ4 peptides flanked by two cysteines residues at both ends. The cysteine residues were added becauses these two peptides were isolated from phage display libraries as circular peptides flanked by two cysteine residues. As these peptides do not represent the natural epitopes but rather mimic them, they are called mimotopes:

```
          9             18            27
5'TGC ATT AAT CAT AGA GGA TAT TGG GTT TGC 3'    (SEQ ID NO:22)
    --- --- --- --- --- --- --- --- --- ---                      ε4
    Cys Ile Asn His Arg Gly Tyr Trp Val Cys     (SEQ ID NO:23)

9             18            27
5'TGC ACA GAT CCT TCT GGA GCA TCT GCA CCT TGC 3' (SEQ ID NO:24)
    --- --- --- --- --- --- --- --- --- --- ---                  TT
    Cys Thr Asp Pro Ser Gly Ala Ser Ala Pro Cys  (SEQ ID NO:25)
```

To achieve this, the cloned protease was cleaved with NheI which is located 50 bp downstream the sequence of the cleavage site of the leader peptide and PvuI, 800 bp further downstream. The DNA sequence coding for the peptide of interest (supra) was inserted between the two restriction sites as two oligonucleotides, which were designed such as to generate the two restriction sites at their ends once they are hybridized. The design of the oligonucleotides took into account that upon ligation to the protease gene the reading frame of the recombinant protein remains open.

The amplification product was cleaved with the restriction enzymes. In both cases the DNA fragments were ligated to the protease gene and introduced by electroporation into *Lactobacillus johnsonii*.

Example 2

Transformation of *Lactobacillus johnsonii*

For transformation purposes *Lactobacillus johnsonii* strain La1 (available from the Institute Pasteur under the accession no. CNCM I-1225) was grown overnight in MRS broth at 37° C. in anaerobic conditions. An aliquot of this culture was used to inoculate (1:10) another culture broth (MRS) containing 0.5 M sucrose. After an additional re-inoculation at 2% into 200 ml MRS+0.5 M sucrose the culture was grown to an $OD_{595}$ of 0.6. The cells were collected by centrifuging at 5000 rpm at 4° C. for 10 minutes, the pellet was washed twice with ½ volume of a solution containing 1M sucrose and 2.5 mM $CaCl_2$, once with ¼ volume of a solution containing 1 M sucrose, 2.5 mM $CaCl_2$) and the pellet obtained after centrifugation was resuspended in 3.5 ml of a solution of 1 M sucrose, 2.5 mM $CaCl_2$+0.459 ml 87% glycerol (10% final concentration). The cells were either directly used for transformation or frozen at −80° C.

For the electroporation 40 εµl of cells were mixed with 10-100 ng of DNA (in <5 µl volume) and transferred into an ice-cold 0.2 cm electroporation cuvette. Pulses at 200 Ω, 25 µF, 2.5 kV in ice-cold 0.2 cm electroporation cuvette were applied. To the cuvette 1 ml of MRS+20 mM $MgCl_2$, 2 mM $CaCl_2$ was added and the suspension was incubated for 2-3 hours at 37° C. 10 µl and 100 µl aliquots, respectively, were plated on MRS agar plates containing the appropriate antibiotic. The plates were incubated anaerobically for 24-48 hours at the same temperature as above. As a selection medium MRS with chloramphenicol (10 µg/ml) was used.

Example 3

Generation of Antisera Against the Proteinase PrtB

To generate antisera against the PrtB rabbits were immunized subcutaneously with *Lactobacillus delbrueckii* subsp. *bulgaricus* strain ATCC11842 expressing proteinase B (PrtB). Bacteria were grown overnight in MRS broth at 42° C. in a GasPak anaerobic system. An aliquot of this culture was used to inoculate another culture broth (MRS) containing 0.5 M sucrose and the culture was grown for 5 hours at 42° C. until an $OD_{595}$ of 0.6. The cells were collected by centrifuging at 5000 rpm at 4° C. for 10 minutes, the pellet was washed twice with 10 ml PBS and then resuspended in 2 ml PBS. Rabbits were immunized three times at two weeks intervals with 1.5 ml PBS resuspended cells and seven days after the last feeding rabbits were bled. Serum was purified six times on $2 \times 10^9$ *Lactobacillus johnsonii* (La1).

Example 4

Generation of Antisera Against the TT and the ε4 Mimotopes

To generate sera against the TT and the ε4 mimotopes rabbits were immunised subcutaneously with either polyoxime-TT mimotope construct or with ε4 mimotope conjugated with keyhole limpet hemocyanin (KLH). Rabbits were immunized four times at two weeks intervals and animals were bled seven days after the last injection. The anti-ε4 serum was purified by immunoaffinity chromatography on CH-Sepharose 4B coupled to ε4 mimotope.

Example 5

Detection of Mimotope-PrtB Fusion Proteins by Antibodies

In order to determine, whether the lactic acid bacteria express the mimotopes in a manner so as to be accessible by and recognized by antibodies, bacteria either containing the PrtB gene without any modification, or containing the recombinant gene (coding either for the ε4 or the TT mimotope respectively) were grown in 25 ml medium containing 10 µg/ml chloramphenicol. Bacterial cells were harvested by centrifugation at 3000×g for 15 minutes at 4° C., washed with 5 ml TBS and recentrifuged. Finally the bacterial pellet was resuspended in 450 µl Tris-buffered saline (TBS: 25 mM Tris/HCl pH 7.5, 0.8% NaCl, 0.02% KCl) and 150 µl 4×non-reducing sample buffer (80 mM Tris/HCl pH 6.8, 2.5% SDS, 0.15% glycerol, 0.05% bromophenol blue). 20 µl aliquots were separated by SDS-polyacrylamide gel electrophoresis (SDS-PAGE) (6% acrylamide-Bis, 0.5M Tris-HCl pH 8.8) and run in a 25 mM Tris, 192 mM glycine buffer (pH 8.3) at 100V for 60 minutes. The gels were stained with BM Fast stain (Boehringer Mannheim, Germany) or transferred electrophoretically onto nitrocellulose membranes (Protran BA 83, Schleicher & Schuell, Dassel, Germany). After transfer the membranes were blocked with PBS/5% BSA for 2 hours at RT. Immunoblots were incubated with either rabbit anti-TT serum (1:1000) or anti-PrtB serum (1:2000) overnight at RT and incubated for 3 hours at RT with a 1:1000 dilution of horseradish peroxidase conjugated goat anti-rabbit IgG. Immunoblots were developed with 4-chloro-1-naphtol for 2 minutes.

As shown in FIG. 1, it could be observed that recombinant *Lactobacillus johnsonii* showed specific bands using the appropriate antibodies for detection, indicating that the ε4 and the TT mimotopes as well as the proteinase PrtB was produced by the recombinant bacteria in the correct conformation.

Example 6

ELISA to Detect Surface Antigen Expression on *Lactobacillus johnsonii* (La1)

Transformed bacteria were grown overnight in 50 ml medium containing 10 µg/ml chloramphenicol. Bacterial cells were harvested by centrifugation at 3000×g for 15 minutes at 4° C., washed with 5 ml TBS and recentrifuged. Finally the bacterial pellet was resuspended in 900 µl TBS and 100 µl 0.5M bicarbonate buffer pH9.6. Costar EIA/RIA half-well plates (Costar, Cambridge, Mass.) were coated overnight at 37° C. with 50 µl bacterial solution per well (approximately $10^8$ bacteria). Coating efficiency was assessed using TTd at a concentration of 10 µg/ml as coating antigen. Plates were extensively washed with PBS/0.1% Tween-20 until no bacteria were left. Wells were blocked in PBS/5% BSA for 2 hours at 37° C. and incubated with 50 µl of either rabbit anti-TT serum or affinity purified rabbit anti-ε4 serum IgG antibodies at a concentration of 10 µg/ml for 4 hours at 37° C. After washing six times with PBS/0.1% Tween-20 plates were incubated 1.5 hours at 37° C. with a 1:1000 dilution of horseradish peroxidase conjugated goat anti-rabbit IgG. Plates were washed six times with PBS/0.1% Tween-20 and developed with tetramethylbenzidine (TMB; Fluka Chemie AG, Buchs, Switzerland). The reaction was stopped with 1M $H_2SO_4$ and absorbance values were measured at 450 nm using an ELISA reader (Molecular devices, Basel, Switzerland).

Figure 2:
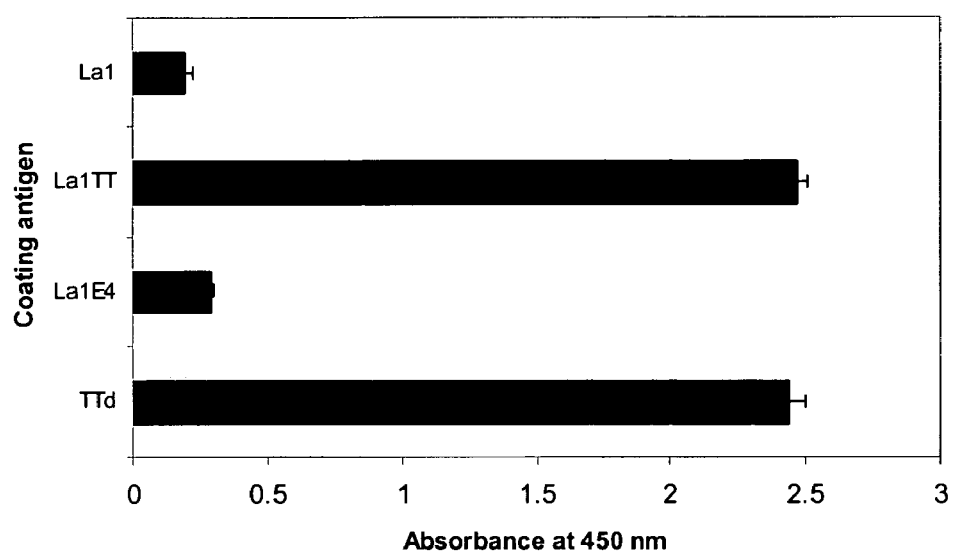
FIG. 2 shows the result of an binding assay of anti TT IgG to surface displayed epsilon mimotopes on lactic acid bacteria in ELISA. Wells were coated with different bacterial clones (approximately $10^8$ bacteria per well) and incubated with rabbit anti-TT serum diluted 1:1000. Tetanus toxoid was coated as a control at a concentration of 10 µg/ml. Binding antibodies were detected with a horseradish peroxidase conjugated goat anti-rabbit IgG (Fc) antibodies.
Figure 3:
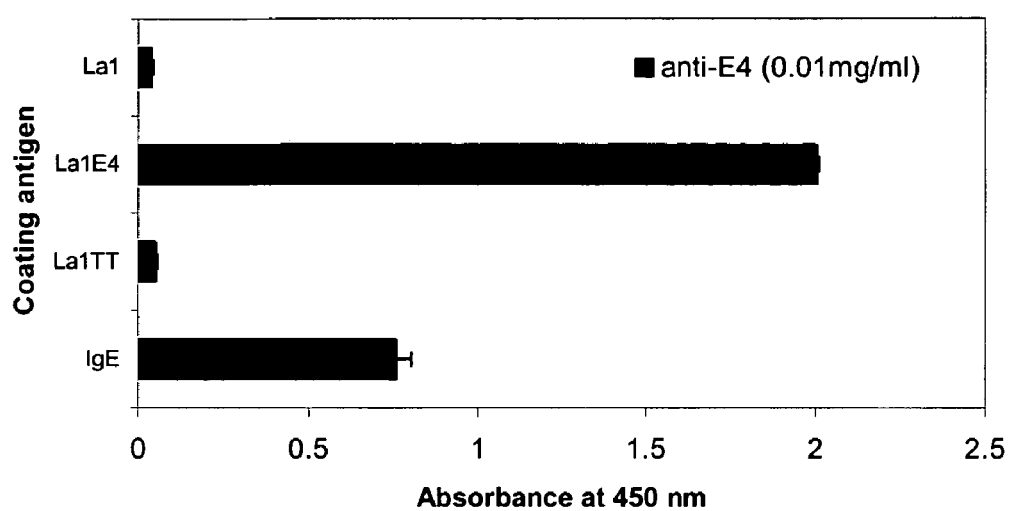
FIG. 3 shows the result of an binding assay of anti-ε4 IgG to surface displayed epsilon mimotopes on lactic acid bacteria in ELISA. Wells were coated with different bacterial clones (approximately $10^8$ bacteria per well) and incubated with affinity purified rabbit anti-ε4 serum (SDS280) at a concentration of 10 g/ml. As control IgE Savazal (10 g/ml) was coated. Binding antibodies were detected using horseradish peroxidase labeled goat anti-rabbit IgG (Fc) antibodies.

As are illustrated in FIGS. 2 and 3 anti-TT and anti-ε4 antibodies specifically recognized the live recombinant La1 expressing TT and ε4 mimotopes indicating that the two mimotopes were expressed and displayed on the cell surface of the bacteria.

What is claimed is:

1. A transformed bacterial strain of the lactic acid bacterium group, expressing a surface polypeptide modified by the insertion of the peptide sequence of SEQ ID NO:25.

2. The bacterial strain according to claim 1, which belongs to a genus selected from the group consisting of *Lactobacillus, Bifidobacterium,* and *Lactococcus.*

3. The bacterial strain according to claim 1 comprising a species selected from the group of *L. acidophilus, L. johnsonhi, L. gasseri, L. casei, L. paracasei* or *L. reuteri.*

4. The bacterial strain according to claim 1, wherein the surface polypeptide is the cell surface anchored protease of *L. bulgaricus.*

5. A food composition containing a bacterial strain according to claim 1.

6. The food composition according to claim 5, which is selected from the group consisting of milk, yoghurt, curd, cheese, fermented milks, milk based fermented products, ice cream, fermented cereal based products, milk based powders, infant formulae and pet food.

7. The food material according to claim 5, wherein the bacterial strain is contained therein in an amount ranging from $10^7$ to $10^{12}$ cfu/dosage form.

8. A pharmaceutical composition containing a bacterial strain according to claim 1.

9. The pharmaceutical composition according to claim 8, wherein the bacterial strain is contained therein in an amount ranging from $10^{10}$ to $10^{12}$ cfu/dosage form.

10. A method of making an ingestible carrier for the treatment of allergy which comprises adding a bacterial strain according to claim 1 to a suitable carrier.

11. The method of claim 10 wherein the suitable carrier is a food composition.

12. The method of claim 11, wherein the food composition is selected from the group consisting of milk, yoghurt, curd, cheese, fermented milks, milk based fermented products, ice cream, fermented cereal based products, milk based powders, infant formulae and pet food.

13. A method for the treatment of allergy which comprises administering to a subject in need of such treatment the food composition of claim 1.

* * * * *

SEQUENCE LISTING

```
<160> NUMBER OF SEQ ID NOS: 25

<210> SEQ ID NO 1
<211> LENGTH: 8
<212> TYPE: PRT
<213> ORGANISM: Homo sapiens

<400> SEQUENCE: 1

Ile Asn His Arg Gly Tyr Trp Val
1               5

<210> SEQ ID NO 2
<211> LENGTH: 8
<212> TYPE: PRT
<213> ORGANISM: Homo sapiens

<400> SEQUENCE: 2

Arg Asn His Arg Gly Tyr Trp Val
1               5

<210> SEQ ID NO 3
<211> LENGTH: 10
<212> TYPE: PRT
<213> ORGANISM: Homo sapiens

<400> SEQUENCE: 3

Arg Ser Arg Ser Gly Gly Tyr Trp Leu Trp
1               5                   10

<210> SEQ ID NO 4
<211> LENGTH: 10
<212> TYPE: PRT
<213> ORGANISM: Homo sapiens

<400> SEQUENCE: 4

Val Asn Leu Thr Trp Ser Arg Ala Ser Gly
1               5                   10
```

-continued

```
<210> SEQ ID NO 5
<211> LENGTH: 10
<212> TYPE: PRT
<213> ORGANISM: Homo sapiens

<400> SEQUENCE: 5

Val Asn Leu Pro Trp Ser Arg Ala Ser Gly
1               5                   10

<210> SEQ ID NO 6
<211> LENGTH: 10
<212> TYPE: PRT
<213> ORGANISM: Homo sapiens

<400> SEQUENCE: 6

Val Asn Leu Thr Trp Ser Phe Gly Leu Glu
1               5                   10

<210> SEQ ID NO 7
<211> LENGTH: 10
<212> TYPE: PRT
<213> ORGANISM: Homo sapiens

<400> SEQUENCE: 7

Val Asn Leu Pro Trp Ser Phe Gly Leu Glu
1               5                   10

<210> SEQ ID NO 8
<211> LENGTH: 10
<212> TYPE: PRT
<213> ORGANISM: Homo sapiens

<400> SEQUENCE: 8

Val Asn Arg Pro Trp Ser Phe Gly Leu Glu
1               5                   10

<210> SEQ ID NO 9
<211> LENGTH: 10
<212> TYPE: PRT
<213> ORGANISM: Homo sapiens

<400> SEQUENCE: 9

Val Lys Leu Pro Trp Arg Phe Tyr Gln Val
1               5                   10

<210> SEQ ID NO 10
<211> LENGTH: 10
<212> TYPE: PRT
<213> ORGANISM: Homo sapiens

<400> SEQUENCE: 10

Val Trp Thr Ala Cys Gly Tyr Gly Arg Met
1               5                   10

<210> SEQ ID NO 11
<211> LENGTH: 7
<212> TYPE: PRT
<213> ORGANISM: Homo sapiens

<400> SEQUENCE: 11

Gly Thr Val Ser Thr Leu Ser
1               5

<210> SEQ ID NO 12
<211> LENGTH: 7
```

```
<212> TYPE: PRT
<213> ORGANISM: Homo sapiens

<400> SEQUENCE: 12

Leu Leu Asp Ser Arg Tyr Trp
1               5

<210> SEQ ID NO 13
<211> LENGTH: 7
<212> TYPE: PRT
<213> ORGANISM: Homo sapiens

<400> SEQUENCE: 13

Gln Pro Ala His Ser Leu Gly
1               5

<210> SEQ ID NO 14
<211> LENGTH: 7
<212> TYPE: PRT
<213> ORGANISM: Homo sapiens

<400> SEQUENCE: 14

Leu Trp Gly Met Gln Gly Arg
1               5

<210> SEQ ID NO 15
<211> LENGTH: 15
<212> TYPE: PRT
<213> ORGANISM: Homo sapiens

<400> SEQUENCE: 15

Leu Thr Leu Ser His Pro His Trp Val Leu Asn His Phe Val Ser
1               5                   10                  15

<210> SEQ ID NO 16
<211> LENGTH: 9
<212> TYPE: PRT
<213> ORGANISM: Homo sapiens

<400> SEQUENCE: 16

Ser Met Gly Pro Asp Gln Thr Leu Arg
1               5

<210> SEQ ID NO 17
<211> LENGTH: 6
<212> TYPE: PRT
<213> ORGANISM: Homo sapiens

<400> SEQUENCE: 17

Val Asn Leu Thr Trp Ser
1               5

<210> SEQ ID NO 18
<211> LENGTH: 126
<212> TYPE: PRT
<213> ORGANISM: Homo sapiens

<400> SEQUENCE: 18

Gln Val Lys Leu Leu Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
                20                  25                  30

Gly Tyr Tyr Trp Thr Trp Ile Arg Gln Arg Pro Gly Lys Gly Leu Glu
            35                  40                  45
```

```
Trp Ile Gly Tyr Ile Tyr Tyr Ser Gly Ser Thr Ser Tyr Asn Pro Ser
        50                  55                  60

Leu Lys Ser Arg Val Thr Met Ser Val Asp Thr Ser Lys Asn Gln Phe
65                  70                  75                  80

Ser Leu Arg Leu Thr Ser Val Thr Ala Ala Asp Thr Ala Val Tyr Tyr
                85                  90                  95

Cys Ala Arg Glu Arg Gly Glu Thr Gly Leu Tyr Pro Tyr Tyr Tyr
                100                 105                 110

Ile Asp Val Trp Gly Thr Gly Thr Thr Val Thr Val Ser Ser
        115                 120                 125

<210> SEQ ID NO 19
<211> LENGTH: 112
<212> TYPE: PRT
<213> ORGANISM: Homo sapiens

<400> SEQUENCE: 19

Glu Leu Val Val Thr Gln Pro Ala Ser Val Ser Gly Ser Pro Gly Gln
1               5                   10                  15

Ser Ile Thr Ile Ser Cys Thr Gly Thr Arg Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Gly Val Phe Gly Gly Gly Thr Lys Leu Thr Val Leu Gly
                100                 105                 110

<210> SEQ ID NO 20
<211> LENGTH: 28
<212> TYPE: DNA
<213> ORGANISM: Artificial
<220> FEATURE:
<223> OTHER INFORMATION: Primer for the promoter of protease gene of
      Lactobacillus bulgaricus

<400> SEQUENCE: 20
ttttgtggat ccttaacttc atagcacg                                       28

<210> SEQ ID NO 21
<211> LENGTH: 27
<212> TYPE: DNA
<213> ORGANISM: Artificial
<220> FEATURE:
<223> OTHER INFORMATION: Primer for the promoter of protease gene of
      Lactobacillus bulgaricus

<400> SEQUENCE: 21
atattatcta gaattgaata gattgcc                                        27

<210> SEQ ID NO 22
<211> LENGTH: 30
<212> TYPE: DNA
<213> ORGANISM: Homo sapiens

<400> SEQUENCE: 22
```

```
tgcattaatc atagaggata ttgggtttgc                                      30

<210> SEQ ID NO 23
<211> LENGTH: 10
<212> TYPE: PRT
<213> ORGANISM: Homo sapiens

<400> SEQUENCE: 23

Cys Ile Asn His Arg Gly Tyr Trp Val Cys
1               5                   10

<210> SEQ ID NO 24
<211> LENGTH: 33
<212> TYPE: DNA
<213> ORGANISM: Homo sapiens

<400> SEQUENCE: 24
tgcacagatc cttctggagc atctgcacct tgc                                  33

<210> SEQ ID NO 25
<211> LENGTH: 11
<212> TYPE: PRT
<213> ORGANISM: Homo sapiens

<400> SEQUENCE: 25

Cys Thr Asp Pro Ser Gly Ala Ser Ala Pro Cys
1               5                   10
```